(12) United States Patent
Horner et al.

(10) Patent No.: US 7,748,567 B2
(45) Date of Patent: *Jul. 6, 2010

(54) SINGLE DOSE DUAL FLUID CARTRIDGE FOR USE WITH HAND-HELD APPLICATORS

(75) Inventors: Terry A. Horner, Allentown, NJ (US); Matthew E. Pappalardo, Leonia, NJ (US)

(73) Assignee: Nordson Corporation, Westlake, OH (US)

( * ) Notice: Subject to any disclaimer, the term of this patent is extended or adjusted under 35 U.S.C. 154(b) by 565 days.

This patent is subject to a terminal disclaimer.

(21) Appl. No.: 11/392,173

(22) Filed: Mar. 29, 2006

(65) Prior Publication Data

US 2007/0228076 A1 Oct. 4, 2007

(51) Int. Cl.
*G01F 11/00* (2006.01)

(52) U.S. Cl. ............... 222/135; 222/145.6; 222/326; 222/327; 222/391

(58) Field of Classification Search .......... 222/325, 222/391, 135–137, 146.6, 326, 327, 390, 222/174, 219, 220, 145.6; 206/219; 433/90
See application file for complete search history.

(56) References Cited

U.S. PATENT DOCUMENTS

| | | | |
|---|---|---|---|
| 999,939 A * | 8/1911 | Wood | 222/388 |
| 2,745,575 A * | 5/1956 | Spencer | 222/327 |
| 2,754,490 A | 7/1956 | Cohen | |
| 3,370,754 A | 2/1968 | Cook et al. | |
| 3,380,451 A | 4/1968 | Porter et al. | |
| 3,437,242 A | 4/1969 | Poitras | |
| 3,477,431 A | 11/1969 | Walecka | |
| 3,595,439 A | 7/1971 | Newby et al. | |
| 3,678,931 A | 7/1972 | Cohen | |
| 3,682,174 A | 8/1972 | Cohen | |
| 3,684,136 A | 8/1972 | Maumann | |
| 3,760,503 A | 9/1973 | Baskas | |
| 3,827,147 A * | 8/1974 | Condon | 433/90 |
| 3,885,710 A | 5/1975 | Cohen | |
| 4,014,463 A | 3/1977 | Hermann | |
| 4,029,236 A | 6/1977 | Carson et al. | |
| 4,159,570 A | 7/1979 | Baskas et al. | |

(Continued)

FOREIGN PATENT DOCUMENTS

DE 19744746 4/1999

(Continued)

OTHER PUBLICATIONS

M. Eberwein, "European Search Report", Aug. 19, 2005, 3 pages.

(Continued)

*Primary Examiner*—Kevin P Shaver
*Assistant Examiner*—Robert K Nichols, II
(74) *Attorney, Agent, or Firm*—Wood, Herron & Evans, L.L.P.

(57) ABSTRACT

A single dose dual fluid cartridge for use with a hand-held applicator is disclosed. With the disclosed dual fluid cartridge, a hand-held applicator may be used to dispense and mix two component end products (e.g. an adhesive). Such an ability to dispense a single dose of a two component end product is especially useful in the dental field.

14 Claims, 6 Drawing Sheets

U.S. PATENT DOCUMENTS

| | | | |
|---|---|---|---|
| 4,538,920 A | | 9/1985 | Drake |
| 4,648,532 A | | 3/1987 | Green |
| 4,693,684 A | * | 9/1987 | Blatherwick et al. .......... 433/90 |
| 4,771,919 A | | 9/1988 | Ernst |
| 4,941,751 A | * | 7/1990 | Muhlbauer ............... 366/182.1 |
| 4,969,747 A | | 11/1990 | Colin et al. |
| 4,986,443 A | | 1/1991 | Saur et al. |
| 5,058,770 A | | 10/1991 | Wolf-Dietrich et al. |
| 5,172,807 A | | 12/1992 | Dragon et al. |
| 5,297,698 A | * | 3/1994 | Martin ......................... 222/95 |
| 5,306,147 A | * | 4/1994 | Dragan et al. ................. 433/90 |
| 5,310,091 A | | 5/1994 | Dunning et al. |
| 5,566,860 A | * | 10/1996 | Schiltz et al. ................ 222/94 |
| 5,871,355 A | * | 2/1999 | Dragan et al. ................ 433/90 |
| 5,924,600 A | * | 7/1999 | Keller ........................ 222/137 |
| 6,047,864 A | * | 4/2000 | Winkler ...................... 222/326 |
| 6,048,201 A | | 4/2000 | Zwingenburger |
| 6,116,900 A | | 9/2000 | Ostler |
| 6,328,715 B1 | | 12/2001 | Dragon et al. |
| 6,398,761 B1 | | 6/2002 | Bills et al. |
| 6,454,129 B1 | | 9/2002 | Green |
| 6,634,524 B1 | | 10/2003 | Helmenstein |
| 6,652,494 B1 | | 11/2003 | Dragon et al. |
| 6,843,652 B2 | | 1/2005 | Xie et al. |
| 6,848,480 B2 | | 2/2005 | Brennan |
| 6,869,419 B2 | | 3/2005 | Dragon et al. |
| 7,237,693 B2 | * | 7/2007 | Brennan et al. ............. 222/327 |
| 7,431,179 B2 | | 10/2008 | Ritter |
| 7,481,333 B2 | | 1/2009 | Goldberg et al. |
| 7,497,355 B2 | | 3/2009 | Horner et al. |
| 7,506,783 B2 | | 3/2009 | Brennan et al. |

FOREIGN PATENT DOCUMENTS

| | | |
|---|---|---|
| DE | 10132417 | 1/2003 |
| FR | 2418173 | 9/1979 |
| WO | WO03050012 | 6/2003 |
| WO | WO2005005305 | 1/2005 |
| WO | 2005/016783 A1 | 2/2005 |

OTHER PUBLICATIONS

D. Jelercic, "European Search Report", Apr. 18, 2006, 3 pages.

* cited by examiner

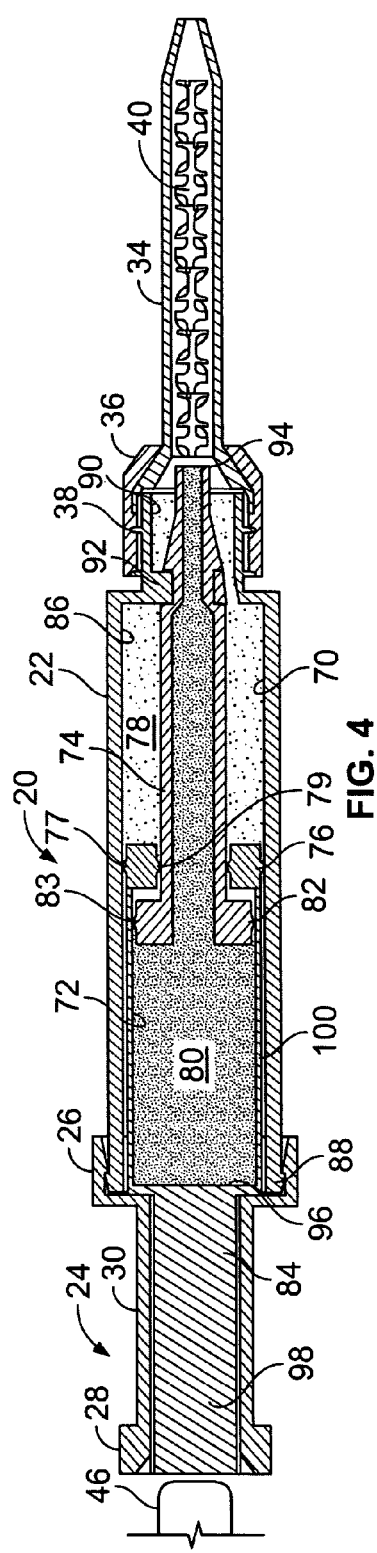
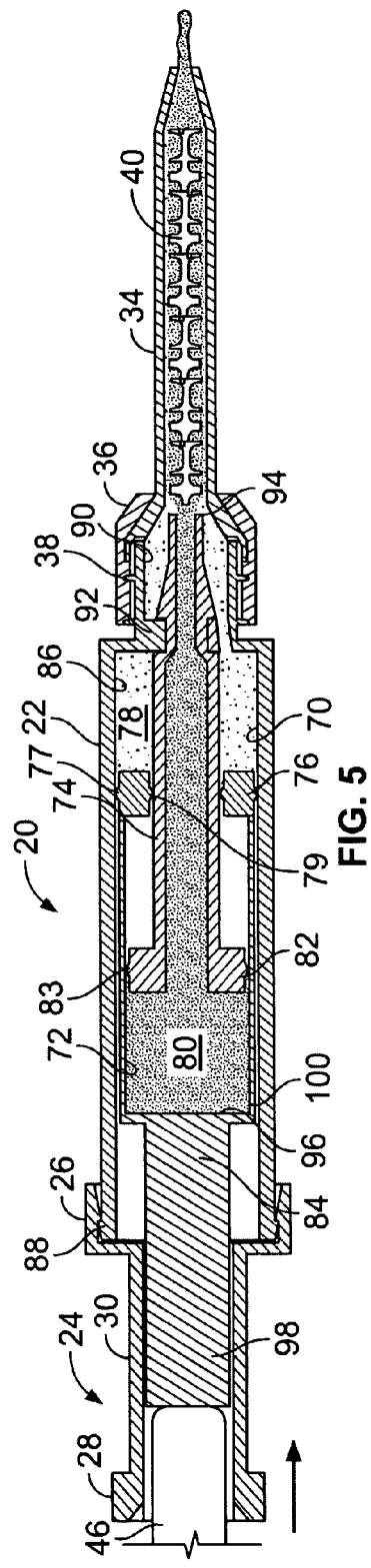
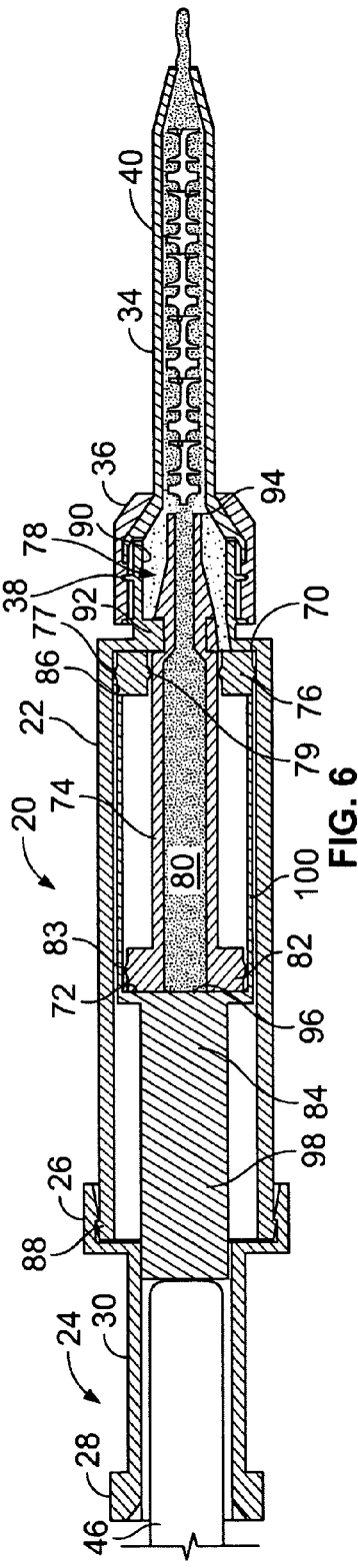
FIG. 4
FIG. 5
FIG. 6

SINGLE DOSE DUAL FLUID CARTRIDGE FOR USE WITH HAND-HELD APPLICATORS

BACKGROUND

In the dental field, dental practitioners prefer using dispensing cartridges that can be disposed of after use with one patient. These are typically referred to as single dose cartridges. Single dose cartridges provide several significant advantages over multi-use cartridges. Single dose cartridges are more sanitary than multi-use cartridges. With a single use cartridge, the dental practitioner can dispose of the cartridge after the procedure is complete, thereby, reducing the possibility of spreading germs and infection among patients. Also, single dose cartridges do not have as mush waste as a multi-use cartridge. With a multi-use cartridge, the resin and hardener components often times cross-contaminate between uses, causing the adhesive to harden and rendering the dispenser useless. The dental practitioner, as a result in this case, is only able to get two to three uses out of the multi-use cartridge and does not achieve the benefit of using the cartridge multiple times.

The single dose dispensing system that many present dental practitioners use consists of a re-usable hand-held applicator and a disposable single component, single dose cartridge that fits into the hand-held applicator. U.S. Pat. Nos. 5,306,147 and 6,095,814 illustrate examples of such single dose dispensing systems. These systems are for dispensing single component fluids. They are not, however, the most appropriate choice when two fluids are required. Presently, a dental practitioner that wants to apply a two component adhesive has to dispense the fluid from the single dose cartridge (e.g. typically the resin) onto a surface and then add a hardener which is then mixed with the resin. This process is time consuming and cumbersome and not the most efficient way for a dental practitioner to mix a two component adhesive.

Accordingly, there is a need for a single dose, two component cartridge that can be used with standard, widely used hand-held applicators.

SUMMARY

According to one aspect of the present invention, a fluid cartridge with a hand-held applicator, wherein the cartridge is formed to store and dispense two fluids, includes an outer cartridge wall defining an outlet, an end cap having a neck that seats in the hand-held applicator, wherein the end cap connects to the outer cartridge wall and defines an open end. The fluid cartridge further includes a delivery tube disposed within the outer cartridge wall which defines an outlet that is co-located with the outlet defined by the outer cartridge wall, a first piston disposed between the outer cartridge wall and the delivery tube forming a first fluid chamber and a second piston disposed within the outer cartridge wall between the first piston and the open end of the end cap. The cartridge also includes a fixed wall disposed between the first piston and the second piston, wherein the fixed wall and the second piston define a second fluid chamber and the cartridge further includes a transmission structure disposed between the second piston to the first piston.

DESCRIPTION OF THE DRAWINGS

These and other features, aspects and advantages of the present invention will become better understood with regard to the following description, appended claims and accompanying drawings where:

FIG. 4 is a longitudinal sectional view of a filled embodiment of a dual fluid cartridge of the present invention, which is depicted along with an attached nozzle and static mixer in section and a portion of the extension of the plunger depicted in FIGS. 2A and 2B;

FIG. 5 is a longitudinal sectional view of the dual fluid cartridge depicted in FIG. 4 in an intermediate dispensing position; and FIG. 6 is a longitudinal sectional view of the dual fluid cartridge depicted in FIG. 4 with the contents of the dual fluid cartridge dispensed.

DETAILED DESCRIPTION

Figure 1A:
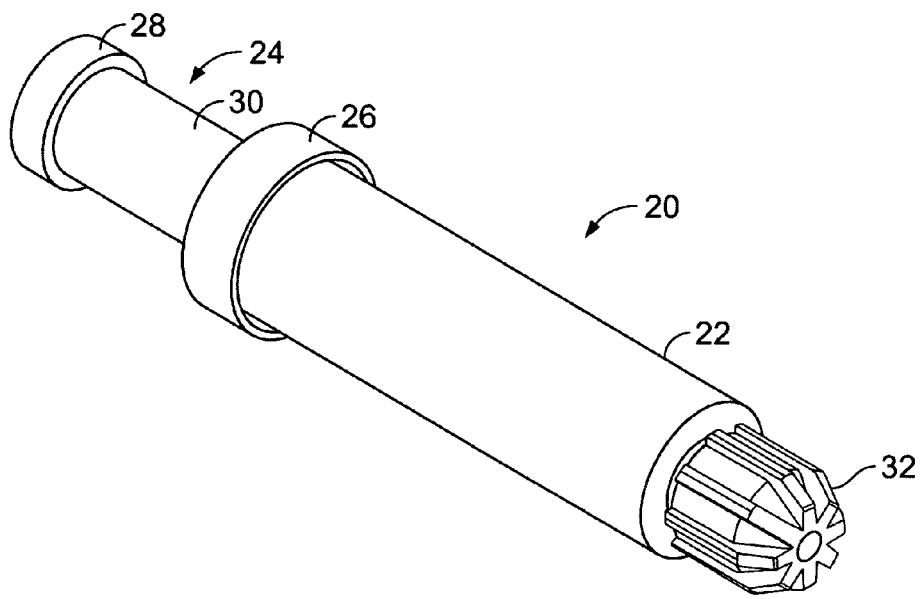
FIG. 1A is a perspective view of an embodiment of a cartridge of the present invention with a cap in place.
Figure 1B:
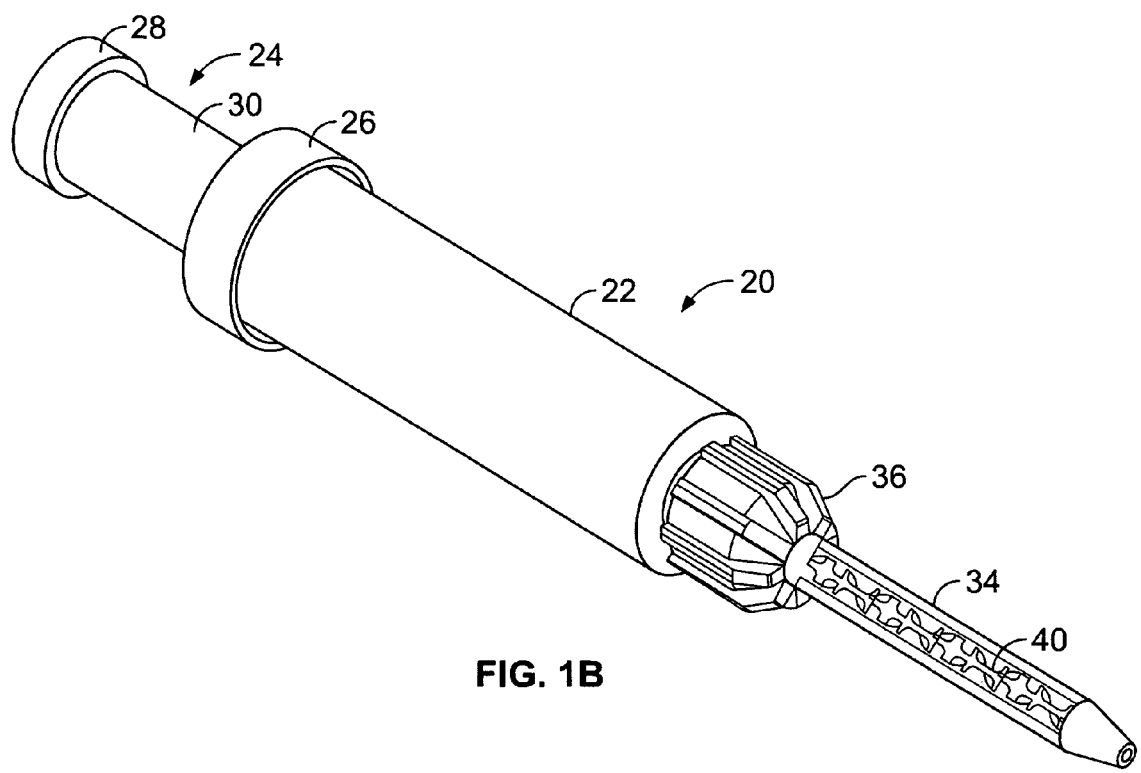
FIG. 1B is a perspective view of an embodiment of a cartridge of the present invention with a mixing element attached.
Figure 2A:
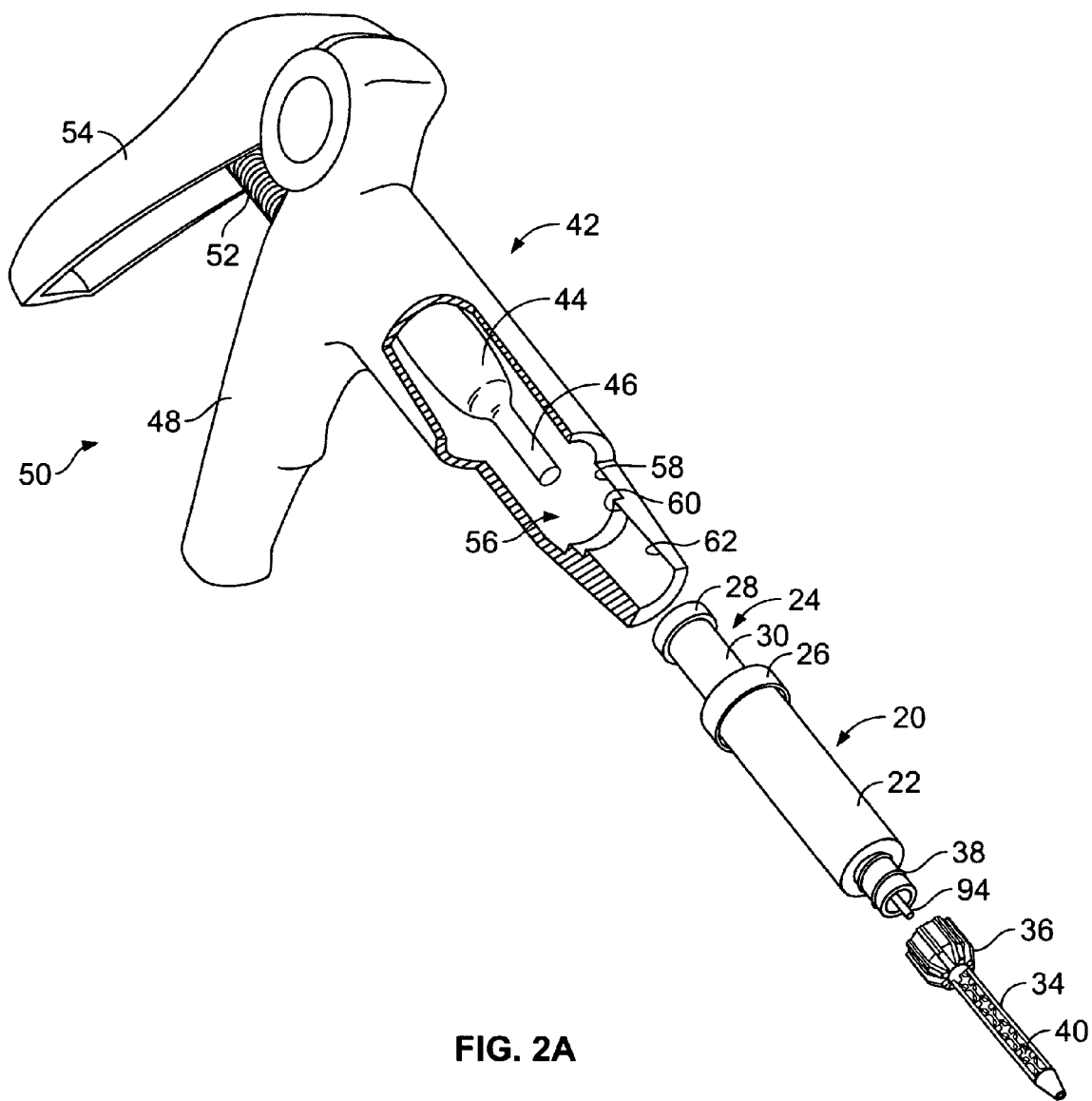
FIG. 2A is a perspective view of a hand-held applicator with the plunger and extension exposed, an embodiment of the cartridge of the present invention and a mixing element.

Referring to FIGS. 1A and 1B, an embodiment of a single dose, dual fluid cartridge 20 of the present invention is depicted. The embodiment depicted is a 1:1 fluid ratio embodiment of the dual fluid cartridge 20, but it should be understood that other embodiments of the cartridge with other fluids ratios (e.g. 2:1 ratio) could be utilized without departing from the invention disclosed herein. The dual fluid cartridge 20 includes an outer cartridge wall 22 and an end cap 24. The end cap 24, in this embodiment, has a snap collar 26 which snaps onto the outer cartridge wall 22. In other embodiments, the end cap 24 may be formed to connect with the outer cartridge wall 22 in a different manner, including having the end cap 24 being formed integral with the outer cartridge wall 22. Further, the end cap 24 includes a seating collar 28 and a neck 30. As explained in detail below, the dual fluid cartridge 20 stores two fluids separate from one another that when mixed together react chemically to form an end product, such as an adhesive. The dual fluid cartridge 20 of this embodiment stores just enough of the component fluids to create a single dose of the end product upon dispensing. FIG. 1A shows the dispensing cartridge 20 with a threaded cap 32 in place. The threaded cap 32 is in place during shipping and prior to use. FIG. 1B shows the dispensing cartridge 20 ready for use with the threaded cap 32 removed and a nozzle 34 attached to the cartridge 20. The nozzle 34 is attached to the cartridge 20 by a retaining nut 36, which is threaded onto a threaded outlet 38 of the cartridge 20 (FIG. 2A). Typically, the nozzle 34 contains a static mixer 40 within it. The static mixer 40 mixes the two fluids stored in the dual fluid cartridge 20 together as they are dispensed from the cartridge 20.

Figure 2B:
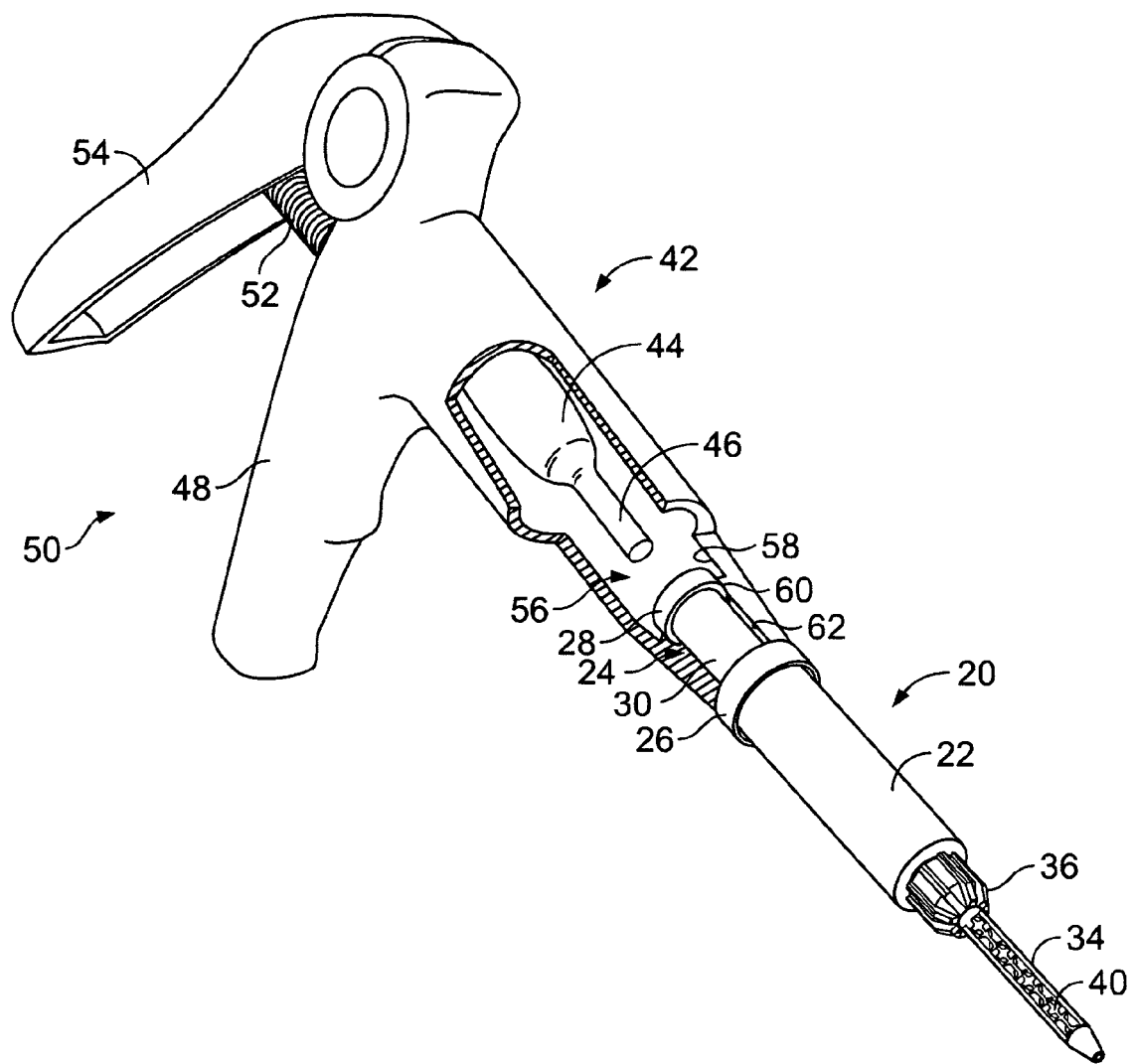
FIG. 2B is a perspective view of a hand-held applicator, in a resting position, with the plunger and extension exposed and having a cartridge inserted with a mixing element attached.
Figure 2C:
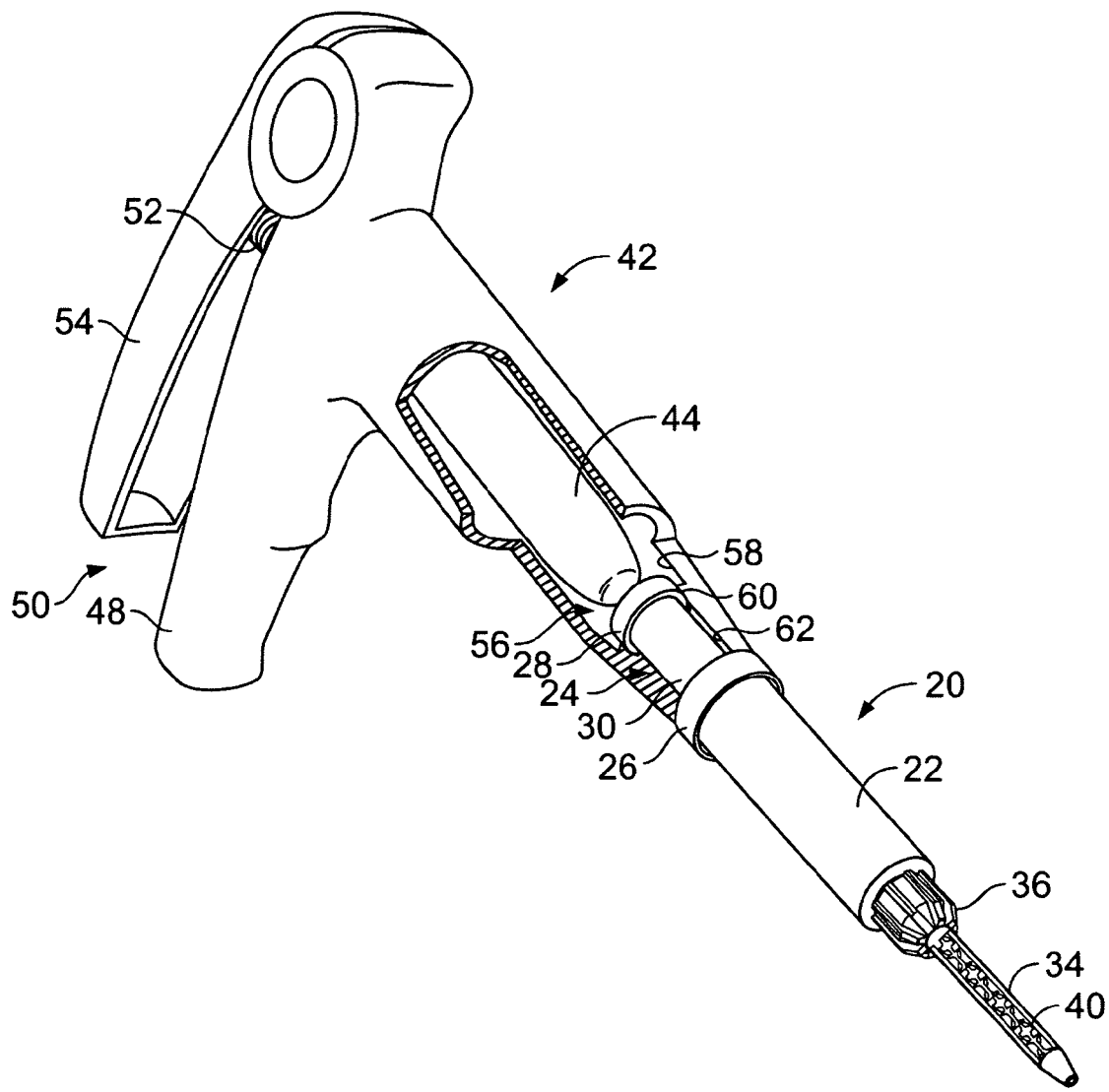
FIG. 2C is a perspective view of a hand-held applicator, in a compressed position, with the plunger exposed and having a cartridge inserted with a mixing element attached.

Referring to FIGS. 2A-2C, the dual fluid cartridge 20 of the present invention is used with a hand-held applicator 42, such as the one depicted in FIGS. 2A-2C. The hand-held applicator 42 is a standard hand-held applicator available in the marketplace. Such hand-held applicators are commonly used in the dental field. It should be understood, however, that the dual fluid cartridge 20 of the present invention is not limited to use in just the dental field. The dual fluid cartridge 20 of the present invention may be used with a hand-held applicator in any field of use. It should also be understood that the cartridge 20 of the present invention may be used with or modified for any hand-held applicator and is not limited to being just used with the one depicted in the figures. The hand-held applicator 42 shown in FIGS. 2A-C has a plunger 44 with an extension 46. The plunger 44 extends back through a front portion 48 of a handle 50 of the hand-held applicator 42. The hand-held applicator 42 also has a plunger channel 56 at the front of the applicator 42 which defines a travel path for the plunger 44 when the applicator 42 is used. The plunger channel 56, at the front end, has three different sections 58, 60, 62 of varying widths to receive and hold the cartridge 20, as explained in more detail below. The back section 58 has the widest width, the middle section 60 is narrower and the front section 62 is the narrowest.

The plunger 44 of the hand-held applicator 42 butts up against a back portion 54 of the handle 50. The portion of the plunger 44 between the front and back portions 48, 54 of the handle 50 is disposed within a spring 52. When a user presses on the back portion 54 of the handle 50, the plunger 44 and the extension 46, through a cam mechanism, are pressed forward in the plunger channel 56, and the spring 52 is compressed (FIG. 2C). When the back portion 54 of the handle 50 is released, the potential energy contained in the spring 52 pushes the plunger 44 and the back portion 54 of the handle 50 back to a resting position (FIG. 2B).

Referring to FIGS. 2A and 2B, in this embodiment, the cartridge 20 is loaded into the applicator 42 by lining up the seating collar 28 with the wide back section 58 of the plunger channel 56 and dropping the cartridge 20 into the plunger channel 56. The cartridge 20 is then pulled forward in the plunger channel 56 so that the seating collar 28 seats in the middle section 60 and the neck 30 of the cartridge 20 sits securely in the narrowest diameter of the front section 62. This is commonly referred to as a "breach-loading" arrangement. The cartridge 20, as depicted in FIG. 2B, is then seated in the applicator 42 and ready for use. It should be understood that the seating arrangement described above is just one way in which the cartridge 20 may be designed to fit in an applicator 42. The end cap 24 may reconfigured in any manner, as necessary, to fit into any intended applicator 42. For example, instead of a breach-loading arrangement, the cartridge 20 may be snapped into plunger channel 56 and be held in place by an interference fit. This is one reason why the end cap 24 is separate from the outer cartridge wall 22 so that differently configured end caps 24 can be used with and snapped onto a standard outer cartridge wall 22 configuration.

Figure 3A:
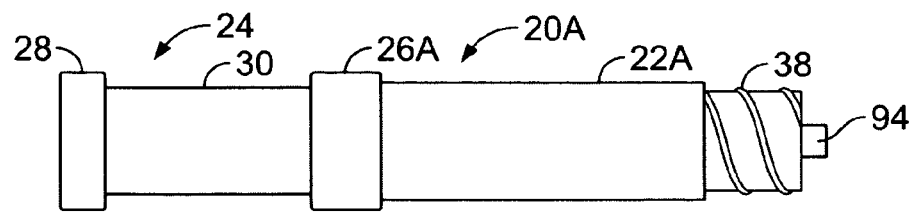
FIGS. 3A-3C are illustrations of varying sizes of cartridges of the present invention.
Figure 3B:
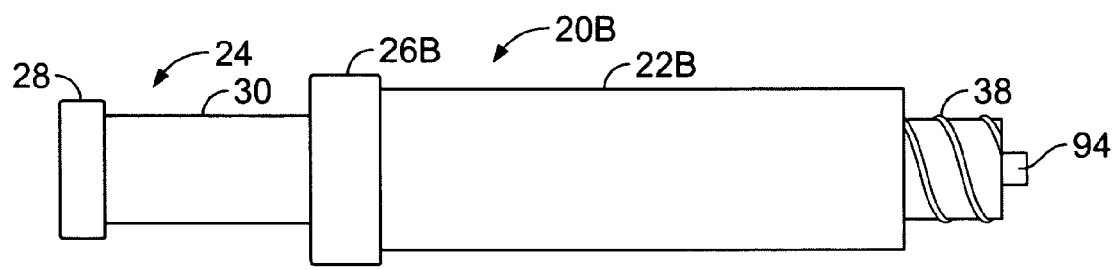
Figure 3C:
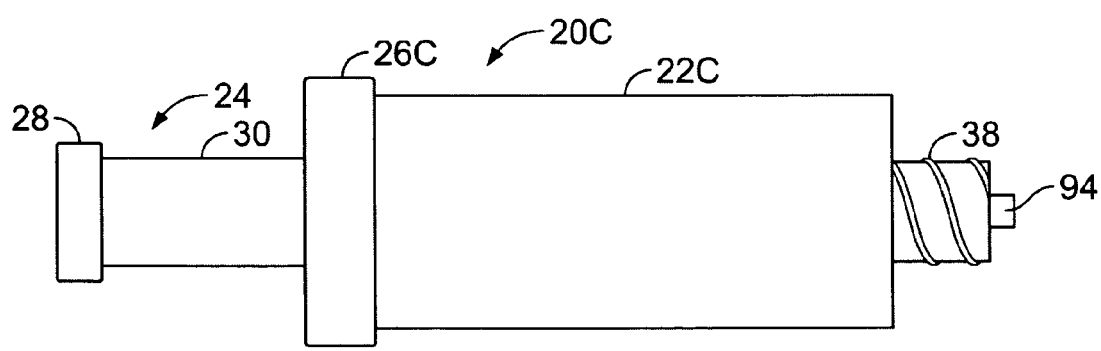

Referring to FIGS. 3A-3C, depending on the amount of end product required, the cartridge 20 may be made of different sizes by adjusting the outer cartridge wall 22 portion of the cartridge 20. For instance, by way of example, the cartridge 20A in FIG. 3A may hold ¼ ml to ⅜ ml; the cartridge 20B in FIG. 3B may hold ¾ ml to 1 ml and the cartridge 20C in FIG. 3C may hold 2 ml to 3 ml. It should noted though that, in this embodiment, no matter what size the outer cartridge wall 22 and the snap collar 26 are formed at, the seating collar 28 and the neck 30 always remain the same size so that they fit into the plunger channel 56 and the seating sections 58, 60 and 62 of the applicator 42.

Referring now to FIG. 4, a longitudinal sectional view of an embodiment of a dual fluid cartridge 20 of the present invention is depicted. This embodiment of the dual fluid cartridge 20 defines a first fluid chamber 70 and a second fluid chamber 72 for storing and dispensing a first fluid 78 and second fluid 80 respectively. In this embodiment of the dual fluid cartridge 20, the cartridge 20, in addition, includes the outer cartridge wall 22, a delivery tube 74, a first piston 76 having an exterior seal 77 and an interior seal 79 and a compression wall 82 having a seal 83. The seals 77, 79, 83 are annular dimples in this embodiment, but it should be understood that other sealing arrangements may be used (e.g. O-rings). The outer cartridge wall 22 in this embodiment is a cylindrical wall defining a hollow interior 86. The outer cartridge wall 22, in this embodiment, at the back end has an annular snap ridge 88. The snap collar 26 of the end cap 24, when the cartridge 20 is assembled, is snapped onto the outer cartridge wall 22 and engages the snap ridge 88. The outer cartridge wall 22 at the other end, the front end, defines a discharge opening 90 and includes the external threaded outlet 38.

The delivery tube 74 of the cartridge 20 is disposed within the hollow interior 86 of the outer cartridge wall 22. In this embodiment, the delivery tube 74 snaps into locking engagement with the outer cartridge wall 22 at a snap connection 92. The delivery tube 74 defines an outlet 94 that extends within and beyond the outlet 90 in this embodiment. It is foreseen that the outer cartridge wall 22 and the delivery tube 74 may also be formed integral with one another, and it is also foreseen that different outlet configurations for the outlets 90, 94 may be adopted other than the one depicted in the figures. The compression wall 82 in this embodiment is formed integral with the delivery tube 74 which fixes the compression wall 82 in place.

The first piston 76 of the dual fluid cartridge 20 is disposed within the cartridge 20 between the exterior of the delivery tube 74 and the interior of the outer cartridge wall 22. In this embodiment, the first piston 76 surrounds the exterior of the delivery tube 74. The first piston 76, in conjunction with the exterior of the delivery tube 74 and the interior of the outer cartridge wall 22, define the first fluid chamber 70.

In this embodiment, the rear piston assembly 84 and the compression wall 82 define the second fluid chamber 72. The delivery tube 74 provides fluid communication between the second fluid chamber 72 and the discharge opening 94. The rear piston assembly 84 includes a rear piston surface 96, a plunger extension 98 and a transmission structure 100. The rear piston assembly 84 in this embodiment does not include a post, but in other embodiments, a post may be used to minimize fluid waste as disclosed in commonly owned U.S. Pat. No. 5,310,091 and U.S. patent application Ser. No. 11/031,929.

Further, it should be understood that the differing portions 96, 98, 100 of the rear piston assembly 84 are all integral with one another in this embodiment, but this is not necessary. One of ordinary skill in the art would understand that it is possible that each portion of the rear piston assembly 84 could be its own separate structure. In this embodiment, the transmission structure 100 extends from the rear piston surface 96 of the rear piston assembly 84, passes snugly between the compression wall 82 and the interior of the outer cartridge wall 22 forming a seal and is in engagement with the first piston 76.

To dispense the fluids from the dual fluid cartridge 20, the rear piston assembly 84 is pressed forward towards the front of the cartridge. In the embodiment described, this is done by actuation of the hand-held applicator 42. Referring to FIG. 2B, in particular, the user presses the rear portion 54 of the handle 50 towards the front portion 48 of the handle 50. As a result, the plunger 44 and extension 46 are pressed forward in the plunger channel 56, in the direction indicated by the arrow in FIG. 5. In this movement, the tip of the extension 46 presses against the plunger extension 98 of the rear piston assembly 84, entering the end collar 24. Simultaneously, the rear piston surface 96 pushes against the fluid 80 stored in chamber 72 and the transmission structure 100 presses against the first piston 76. The fluid 80 being pushed by the rear piston surface 96 in the chamber 72 gets compressed by the fixed compression wall 82, pushing the fluid 80 through the delivery tube 74 and through the discharge opening 94, where the fluid 80 is discharged from the dual fluid cartridge 20. At the same time, the pressing of the transmission structure 100 against the first piston 76 causes the fluid 78 in the first fluid chamber 70 to be pressed into the discharge opening 90, through which the fluid 78 is discharged from the dual fluid cartridge 20. As the fluids 78, 80 are discharged from the dual fluid cartridge 20 through the discharge openings 90, 94, they are mixed together by the static mixer 40 in the nozzle 34.

This fluid discharge and mixing process continues as long as the plunger 44 and extension 46 are being actuated and as long as fluids are still left to be dispensed from the dual fluid cartridge 20. FIG. 5 depicts the dual fluid cartridge 20 in an intermediate dispensing position with a portion of the fluids 78, 80 dispensed from the dual fluid cartridge 20. FIG. 6 depicts the dual fluid cartridge 20 with the fluid contents of the chambers 70, 72 of the cartridge 20 fully dispensed.

The arrangement of the dual fluid cartridge 20 in FIG. 6, minus the waste fluids 78, 80 shown remaining, is how the dual fluid cartridge 20 looks prior to being filled. To fill the dual fluid cartridge 20, the chambers 70, 72 are filled with the appropriate fluids 78, 80 through their respective discharge openings 90, 94. The filling process occurs in the reverse manner of the dispensing process described above. During the filling process, air can get trapped in the chambers 70, 72 between the incoming fluids 78, 80 and the piston surfaces 76, 96. Air trapped in the chambers 70, 72 can cause a number of problems in the use of the dual fluid cartridge 20. Most significantly, air trapped in chambers 70, 72 can negatively impact the ability to control the volumetric dispensing ratio of the fluids 78, 80 in the chambers 70, 72. To alleviate this problem, an air venting system may be employed, such as the air venting system described in commonly owned international patent application number PCT/US03/17997 or U.S. patent application Ser. Nos. 10/755,796 and 11/031,929, which are incorporated by reference herein.

It should be understood that many differing embodiments of the dual fluid cartridge 20 of the present invention may be designed and employed.

While the invention has been discussed in terms of certain embodiments, it should be appreciated that the invention is not so limited. The embodiments are explained herein by way of example, and there are numerous modifications, variations and other embodiments that may be employed that would still be within the scope of the present invention.

What is claimed is:

1. A fluid cartridge for use with a hand-held applicator including an extendable plunger, wherein the cartridge is formed to store and dispense two fluids, comprising:
   an outer cartridge wall having an inner diameter, proximal and distal ends, and a first outlet at the distal end;
   an end cap having a neck that seats in the hand-held applicator, the end cap including a connecting collar that connects to the outer cartridge wall at the proximal end and defines an open end, the neck having a reduced inner diameter relative to the inner diameter of the outer cartridge wall;
   a delivery tube disposed within the outer cartridge wall and defining a second outlet at the distal end;
   a first piston disposed between the outer cartridge wall and the delivery tube forming a first fluid chamber;
   a second piston disposed within the outer cartridge wall between the first piston and the open end of the end cap;
   a piston extension projecting in a proximal direction from the second piston and disposed within the neck, the piston extension adapted to engage the extendable plunger when the extendable plunger enters the neck;
   a fixed wall disposed between the first piston and the second piston, wherein the fixed wall and the second piston define a second fluid chamber; and
   a transmission structure disposed between the second piston and the first piston.

2. The fluid cartridge for use with a hand-held applicator of claim 1, wherein the end cap includes a seating collar adapted to seat within the hand-held applicator.

3. The fluid cartridge for use with a hand-held applicator of claim 2, wherein the cartridge is designed to load into a hand-held applicator in a breach loading manner.

4. The fluid cartridge for use with a hand-held applicator of claim 2, wherein the cartridge is designed to snap into a hand-held applicator.

5. The fluid cartridge for use with a hand-held applicator of claim 1, wherein the end cap is formed integral with the outer cartridge wall.

6. A fluid cartridge for use with a hand-held applicator including an extendable plunger, wherein the cartridge stores and dispenses first and second fluids, comprising:
   an outer cartridge wall having an inner diameter, proximal and distal ends, and a first outlet at the distal end;
   an end cap having a neck that seats in the hand-held applicator, the end cap including a connecting collar that connects to the outer cartridge wall at the proximal end and defines an open end, the neck having a reduced inner diameter relative to the inner diameter of the outer cartridge wall;
   a delivery tube disposed within the outer cartridge wall and defining a second outlet at the distal end;
   a first piston disposed between the outer cartridge wall and the delivery tube forming a first fluid chamber that contains the first fluid;
   a second piston disposed within the outer cartridge wall between the first piston and the open end of the end cap;
   a piston extension projecting in a proximal direction from the second piston and disposed within the neck, the piston extension adapted to engage the extendable plunger when the extendable plunger enters the neck;
   a fixed wall disposed between the first piston and the second piston, wherein the fixed wall and the second piston define a second fluid chamber that contains the second fluid; and
   a transmission structure disposed between the second piston and the first piston.

7. The fluid cartridge for use with a hand-held applicator of claim 6, wherein the end cap includes a seating collar adapted to seat within the hand-held applicator.

8. The fluid cartridge for use with a hand-held applicator of claim 7, wherein the cartridge is designed to load into a hand-held applicator in a breach loading manner.

9. The fluid cartridge for use with a hand-held applicator of claim 7, wherein the cartridge is designed to snap into a hand-held applicator.

10. The fluid cartridge for use with a hand-held applicator of claim 6, wherein the end cap is formed integral with the outer cartridge wall.

11. The fluid cartridge for use with a hand-held applicator of claim 6, wherein the cartridge contains an amount of the first fluid and the second fluid to prepare a single dose of an end product formed with the first and second fluids.

12. A single dose fluid dispensing mechanism, comprising:
a hand-held applicator including an extendable plunger;
a dual fluid cartridge disposed in the hand-held applicator, wherein the dual fluid cartridge includes:
   an outer cartridge wall having an inner diameter, proximal and distal ends, and a first outlet at the distal end;
   an end cap having a neck that seats in the hand-held applicator, the end cap including a connecting collar that connects to the outer cartridge wall at the proximal end and defines an open end, the neck having a reduced inner diameter relative to the inner diameter of the outer cartridge wall;
   a delivery tube disposed within the outer cartridge wall and defining a second outlet at the distal end;
   a first piston disposed between the outer cartridge wall and the delivery tube forming a first fluid chamber that contains a first fluid;
   a second piston disposed within the outer cartridge wall between the first piston and the open end of the end cap;
   a piston extension projecting in a proximal direction from the second piston and disposed within the neck, the piston extension adapted to engage the extendable plunger when the extendable plunger enters the neck;
   a fixed wall disposed between the first piston and the second piston, wherein the fixed wall and the second piston define a second fluid chamber that contains a second fluid; and
   a transmission structure disposed between the second piston and the first piston.

13. The single dose fluid dispensing mechanism of claim 12, wherein the first fluid and the second fluid in the fluid dispensing mechanism are components of a dental end product.

14. A method of dispensing a single dose of a two component end product, comprising:
   a. providing a hand-held applicator having a plunger;
   b. providing a dual fluid cartridge which includes:
      i. an outer cartridge wall having an inner diameter, proximal and distal ends, a first outlet at the distal end;
      ii. an end cap having a neck that seats in the hand-held applicator, the end cap including a connecting collar that connects to the outer cartridge wall at the proximal end and defines an open end, the neck having a reduced inner diameter relative to the inner diameter of the outer cartridge wall;
      iii. a delivery tube disposed within the outer cartridge wall and defining a second outlet at the distal end;
      iv. a first piston disposed between the outer cartridge wall and the delivery tube forming a first fluid chamber that contains a first fluid;
      v. a second piston disposed within the outer cartridge wall between the first piston and the open end of the end cap;
      vi. a piston extension projecting in a proximal direction from the second piston and disposed within the neck, the piston extension adapted to engage the plunger when the plunger enters the neck;
      vii. a fixed wall disposed between the first piston and the second piston, wherein the fixed wall and the second piston define a second fluid chamber that contains a second fluid; and
      viii. a transmission structure disposed between the second piston and the first piston;
   c. attaching a mixing element to the dual fluid cartridge;
   d. inserting the reduced diameter neck of the dual fluid cartridge with the attached mixing element into the hand-held applicator; and
   e. actuating the plunger of the hand-held applicator, wherein the plunger enters the neck and contacts the piston extension of the dual fluid cartridge which presses the second piston, which presses the transmission structure, which presses the first piston and pushes the first and second fluids contained in the cartridge out of the mixer and through the attached mixing element.

* * * * *